United States Patent [19]

Rand et al.

[11] Patent Number: 5,053,215

[45] Date of Patent: Oct. 1, 1991

[54] NMR-ASSAYABLE LIGAND-LABELLED TRIFLUOROTHYMIDINE CONTAINING COMPOSITION AND METHOD FOR DIAGNOSIS OF HSV INFECTION

[75] Inventors: Kenneth H. Rand; Nicholas S. Bodor; Wallace Brey, all of Gainsville, Fla.

[73] Assignee: University of Florida, Gainesville, Fla.

[21] Appl. No.: 199,354

[22] Filed: May 26, 1988

[51] Int. Cl.$^5$ ................... A61K 43/00; A61K 49/02
[52] U.S. Cl. ........................... 424/1.1; 424/9; 436/173; 436/806; 435/5
[58] Field of Search ............ 424/9, 1.1; 436/173, 436/806, 808, 547, 548, 507; 435/7

[56] References Cited

U.S. PATENT DOCUMENTS 3,201,387  8/1965  Heidelberger ............... 544/309 X
4,210,638  7/1980  Goeer ............................ 514/49
4,675,287  6/1987  Reisfeld ........................ 435/7

OTHER PUBLICATIONS

Rand et al., "Trifluorothymidine: Potential Non-Invasive Diagnosis of Herpes Simplex Infection . . . ", J. Virol. Methods 18, 257-270 (1987).
Chemical Abstracts, vol. 108(13), Abst. 109067b, p. 319, 3/28/88, Hand et al., "Trifluorothymidine: Potential Non-Invasive Diagnosis of Herpes Simplex Infection . . . ", J. Virol. Methods 18(4), 257-69 (1987).
Fischer et al., *Mol. Pharmacol.*, vol. 24, No. 1, "Preferential Inhibition of 5-Trifluoromethyl-2'-Deoxyuridine Phosphorylation by 5'-Amino-5'-Deoxythymidine in Uninfected Versus Herpes Simplex Virus-Infected Cells", pp. 90-96 (Jul. 1983).

*Primary Examiner*—Sam Rosen
*Attorney, Agent, or Firm*—Kerkam, Stowell, Kondracki & Clarke

[57] ABSTRACT

A method for diagnosing HSV infections in human or non-human patients which involves intravenously administering to the patient a non-invasively assayable ligand-labelled anti-viral drug, wherein the drug is a compound which is phosphorylated bby the HSV-induced thymadine kinase present in HSV-infected cells to a phosphorylated assayable ligand-labelled compound which cannot diffuse from within the infected cells and then non-invasively assaying the presence or absence of the accumulated phosphorylated compound present therein.

A pharmaceutical composition in intravenously administrable form and adapted for the diagnosis of HSV infection which is a mixture of a non-invasively assayable ligand-labelled anti-viral drug and a pharmaceutically acceptable carrier therefor.

3 Claims, 2 Drawing Sheets

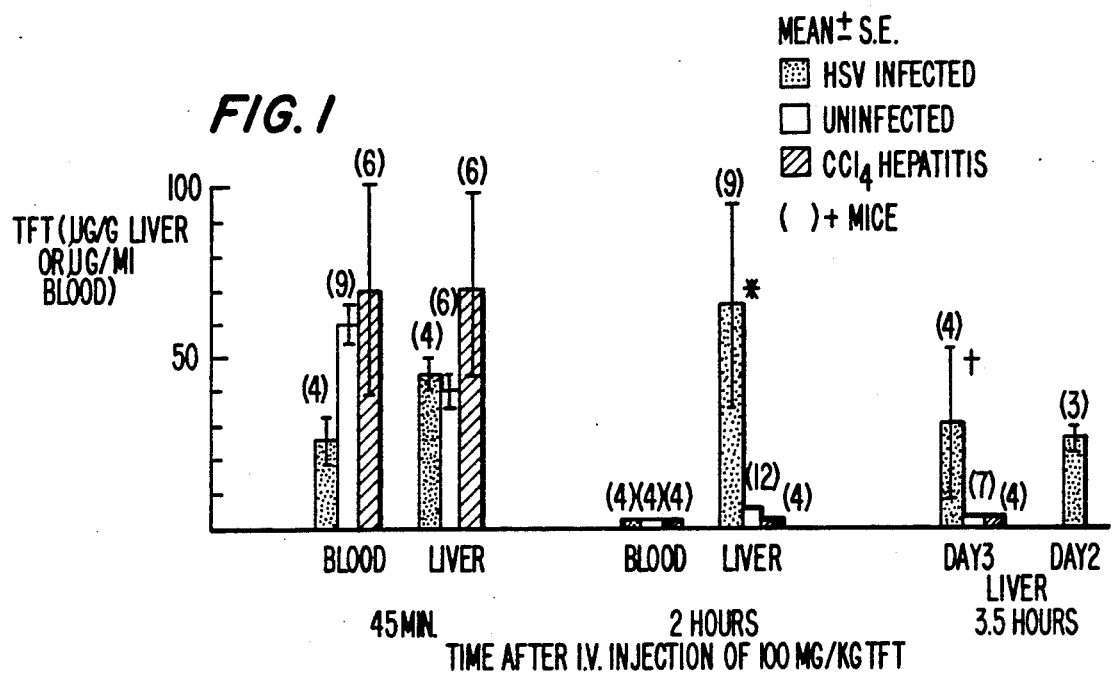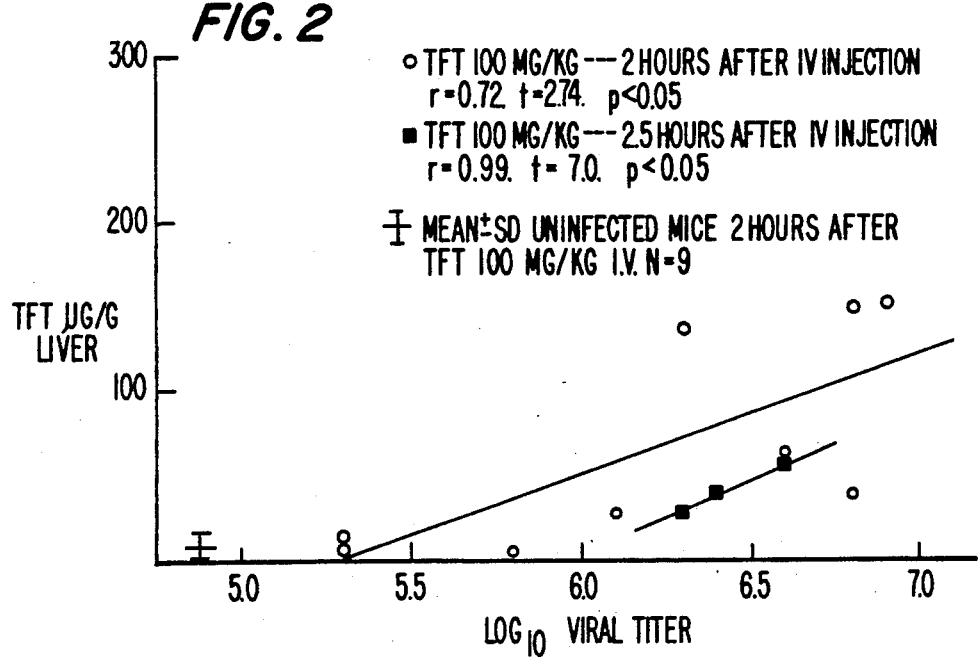

NMR-ASSAYABLE LIGAND-LABELLED TRIFLUOROTHYMIDINE CONTAINING COMPOSITION AND METHOD FOR DIAGNOSIS OF HSV INFECTION

The research leading to the present invention was supported in part by the U.S. Government, specifically by the Veterans Administration and NIH Grant No. IROI EYO5800.

BACKGROUND OF INVENTION

1. Field of the Invention

The present invention relates to a method and composition for diagnosis of HSV infections in animals and humans.

2. Prior Art

Herpes Simplex infections (HSV) in humans and animals are exceedingly common. Approximately 75% of the adult population has been infected with HSV-1 and some 30-50% experience recurrent oral cold sores as the sole manifestation of infection with the remainder having no symptoms. Similarly, although HSV-2 or genital herpes is extremely prevalent, and also recurs frequently; its major significance is less in terms of physical discomfort and more in terms of emotional upset and interference with sex life. However, a small number of patients develop life threatening encephalitis or disseminated infection. Despite sophisticated instrumentation, HSV encephalitis cannot be reliably diagnosed without a brain biopsy and disseminated infection in the newborn is likewise undiagnosable unless skin infection occurs, which would be clinically obvious.

There presently exists no efficient, reliable, non-invasive method for diagnosing visceral HSV infections in animals and humans.

It is an object of the present invention to provide a non-invasive method and composition for the rapid, efficient and reliable diagnosis of HSV infections in animals and humans.

SUMMARY OF THE INVENTION

The above and other objects are realized by the present invention which provides a method for the diagnosis of a HSV infection in a human or non-human patient in need thereof comprising intravenously administering to the patient a non-toxic amount of a non-invasively assayable ligand-labelled anti-viral drug; the drug comprising a compound which is phosphorylated by the HSV-induced thymidine kinase present in HSV-infected cells to the phosphorylated assayable ligand-labelled compound which is substantially non-diffusible from within the HSV-infected cells and non-invasively assaying the presence or absence of the accumulated phosphorylated assayable ligand-labelled compound in the cells.

An additional embodiment of the invention comprises a pharmaceutical composition in non-toxic, unit dosage, intravenously administrable form adapted for the diagnosis of a HSV infection in a human or non-human patient in need thereof comprising a non-invasively assayable ligand-labelled anti-viral drug comprising a compound which is phosphorylated by the HSV-induced thymidine kinase present in HSV-infected cells to a phosphorylated assayable ligand-labelled compound which is substantially non-diffusible from within the HSV-infected cells and a pharmaceutically acceptable carrier therefor.

DETAILED DESCRIPTION OF THE INVENTION

Figure 3A:
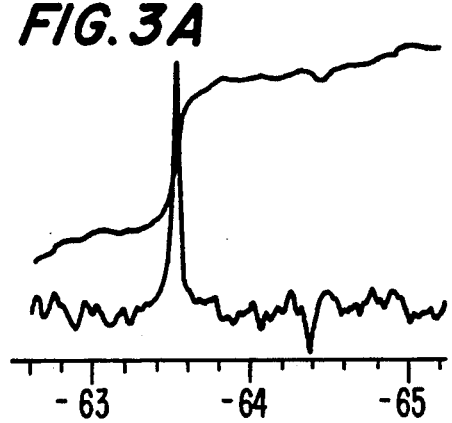
Figure 3B:
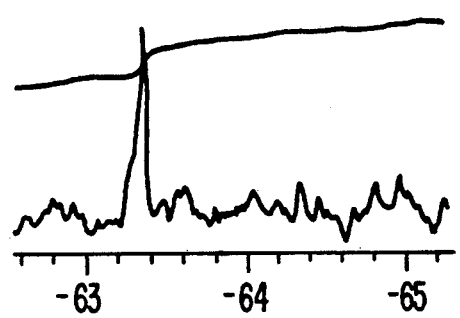
Figure 3C:
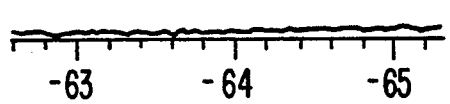
Figure 3D:
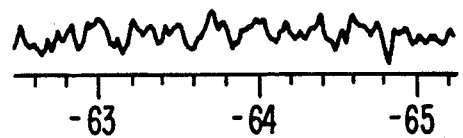

A number of anti-viral drugs exhibit marked accumulation in HSV infected cells in vitro. The virus induced enzyme thymidine kinase (TK) phosphorylates these drugs to the monophosphate, which is converted to the di and the triphosphate by cellular enzymes. This mechanism has been shown to lead to the intracellular accumulation of acyclovir [Furman et al, Antimicro. Agents Chemother., Vol. 20, pp. 518-524 (1981)], 9-(2-Hydroxyethoxymethyl) guanine (DHPG) [Smee et al, Biochem. Pharmacol., Vol. 34, pp. 1049-1056 (1985)], trifluorothymidine (TFT) [Fischer et al, Mol. Pharmacol., Vol. 24, pp. 90-96 (1983), and others [Price et al, Human Herpesvirus Infections: Pathogenesis, Diagnosis and Treatment, In: Lopez et al (eds.) Raven Press, New York, N.Y., pp. 227-233 (1986)].

The literature contains contradictory data regarding HSV specific concentration of antiviral drugs in HSV infected tissues. Price et al Human Herpesvirus Infections: Pathogenesis, Diagnosis and Treatment. In: Lopez et al (eds.) Raven Press, New York, N.Y., pp. 227-233 (1986); Biochem. Pharmacol., Vol. 32, pp. 2455-61 (1983)] and Saito et al [Science, Vol. 217, pp. 1151-1153 (1982); Ann. Neurol. Vol. 15, pp, 548-558 (1984)] using $^{14}C$ labeled 2' fluoro-5-methyl-1-$\beta$-D-arabinosyluracil (FMAU) were able to show specific concentration of the drug in the optic nerve and chiasm of rats after intraocular inoculation of HSV-1. However, there is also non-specific accumulation of FMAU in the choroid plexus and the cells lining the ventricular walls. Biron et al [Antimicrob. Agents Chemother., Vol. 21, pp. 44-50 (1982)] studied $^{14}C$ labeled acyclovir, which has been shown to accumulate intracellularly in HSV infected cells in vitro [Furman et al, supra]. Following s.c. injection, acyclovir levels were similar in all HSV infected and uninfected tissues studied, i.e., liver, kidney, spleen, lung, blood and brain. Price et al were also unable to demonstrate any selective accumulation of acyclovir in HSV infected tissues in vivo [Price et al, supra]. It is difficult to reconcile the lack of accumulation of acyclovir in HSV infected tissues, with the observation herein of high levels of TFT in livers from HSV-2 infected mice, since both compounds are phosphorylated by the HSV TK and do accumulate in tissue culture.

Recently, Smee et al showed that while acyclovir accumulated in the form of phosphorylated intermediates in HSV infected cells, in vitro, it was also rapidly degraded back to acyclovir, and diffused out of the cell Smee et al, supra]. In contrast, DHPG also accumulated in a similar manner, but did not hydrolyze back to the parent compound as readily. Thus, even related drugs which utilize the some basic steps in their mechanism of action can behave quite differently biologically. Furthermore, i.v. injection of TFT via the jugular vein is used herein, which would result in extremely high blood levels initially, with a rapid fall off, as was observed, i.e., no detectable drug at 2 hours in the blood. When TFT was given by i.p. injection, it was impossible to demonstrate accumulation of TFT in the liver of HSV infected mice. Since Biron et al used s.c. injection, and since plasma levels remained reasonably elevated for 2 hours or more after injection, it is possible that the "depot" effect of s.c. injection, together with the propensity of phosphorylated acyclovir to be rapidly hydrolyzed back to the parent compound, was responsible for the lack of accumulation. Another difference between the present invention and the system of Biron et al is that herein drug levels were measured on day 2 or 3 after infection while their drug studies were carried out on days 4–5 after infection. It is very possible that the relationship between drug accumulation and level of infection changes during the course of the infection, and some preliminary observations in this regard are discussed below.

The present invention is predicated on the discovery that this phenomenon of accumulation of anti-viral drug metabolites in HSV-infected cells may be utilized to effectively and non-invasively diagnose HSV infections in humans and non-humans.

According to the present invention, a non-invasively or externally assayable ligand labelled derivative of the drug is intravenously administered to the patient and, following diffusion into and phosphorylation into non-diffusible derivatives and accumulation thereof in any HSV infected cells and then externally assayed to detect the presence or absence of the accumulation.

The ligand may be any conventional assayable ligand which does not render the drug or metabolite thereof toxic or unable to accumulate.

For example, TFT contains 3 fluorine atoms which comprise approximately 19% of its molecular weight. Since the naturally occurring isotope, $^{19}F$ has a nuclear spin of $\frac{1}{2}$, sufficient concentrations of TFT can be detected by nuclear magnetic resonance spectroscopy. TFT concentrates in the tissues of HSV-2 infected animals thereby rendering the excess accumulation detectable, non-invasively, by $^{19}F$ NMR spectroscopy.

The method and composition of the invention are suitable for the diagnosis of HSV infection in human or non-human animals. The drug may be admixed with any suitable intravenously administrable carrier. Suitable carriers include physiologic saline, isotonic dextrose, isotonic buffers such as sodium hydrogen phosphate ($NaH_2PO_4$, $Na_2HPO_4$) with ethyl alcohol, propylene glycol, benzyl alcohol, etc.

The drug is compounded with the carrier in unit dosage, i.v., administrable form in non-toxic amounts which will vary, depending upon the compound employed. It is only necessary to include an amount of compound in the composition which will accumulate in its metabolized form in the HSV-infected cells of the patient in amounts detectable by the assay procedure chosen. Again, the amounts will vary, depending upon the assayable ligand utilized and the particular assay method chosen.

The invention is illustrated by the following non-limiting examples:

EXAMPLE 1

Because TFT crosses the blood brain barrier poorly, TFT concentrations were measured in the livers of mice with hepatitis due to HSV-2 infection. For comparison, TFT levels were measured in the livers of uninfected mice and mice with carbon tetrachloride ($CCl_4$) induced hepatitis.

HSV-2 (333 strain) was grown and titered in Vero cells as previously described [Rand -t al, J. Med. Virol., Vol. 20, pp. 1–8 (1986).

The following strains of mice were obtained from the National Cancer Institute: Balb/c, CBA/J, A/HeN, A/J, P/N, and DBA/2N. Preliminary studies showed that the DBA/J strain consistently yielded the highest titers in the liver following intraperitoneal injection of the 333 strain of HSV-2. All further studies were therefore done with CBA/J mice, aged 4–6 weeks, weighing 18–23 g.

Carbon tetrachloride was dissolved in olive oil for injection. Trifluorothymidine was assayed by high pressure liquid chromatography (HPLC).

4–6 week old, 18–23 gm, CBA/J mice were injected intraperitoneally (i.p.) with 1.5 ml of HSV-2 ($2-4\times10^6$ pfu/ml). In this model, maximal viral titers are present in the liver between days 3 and 5, and mice generally died from day 4 to 6 from this high inoculum. Three days after infection, mice were anesthetized with a 3:1 mixture of 100 mg/ml ketamine HCl:20 mg/ml Xylazine at a dose of 0.2 ml/kg. The jugular vein was surgically exposed, and mice were injected intravenously with 100 or 160 mg/kg of TFT in the appropriate volume of a 20 mg/ml solution in Phosphate Buffered Saline (PBS) pH 7.4. Mice were sacrificed at 45 minutes, 2 hours, 2.5 and 3.5 hours after I.V. injection of TFT. The livers were immediately excised and frozen at $-70°$ C. until they could be studied. For viral titration and measurement of TFT, 1.5 ml of phosphate buffered saline pH 7.4 was mixed with 1 g of liver and the mixture homogenized (10 strokes using a Pyrex Ten Broeck tissue grinder), followed by sonication $\times 4$ for 30 sec. in a Fisher 300 sonic dismembrator at a relative output of 0 55; 0.8 ml of the liver homogenate was mixed with an equal volume of methanol, vortexed extensively and then centrifuged at $15,000\times g$ for 15 minutes. The supernatant was analyzed by HPLC for TFT and the results expressed per gram of liver after correction for dilution. Prior to sonication, 0.5 ml of the liver homogenate was serially diluted in serum free tissue culture media and titrated in triplicate in Vero cells as previously described [Rand et al, supra]. In some experiments the clarified supernatant that had been mixed with methanol as described above was placed in a 5 mm NMR tube and $^{19}F$ content measured by NMR spectroscopy. In other experiments the entire liver was excised, and placed in a 12 mm NMR tube and the $^{19}F$ directly analyzed by NMR spectroscopy.

Carbon tetrachloride was selected as a control for hepatitis because previous work suggested that the dose related hepatic toxicity was limited to the liver and did not involve the kidney which might conceivably alter the pharmacokinetics of TFT. $CCl_4$ induces a dose dependent patchy, centrilobular necrosis which is analogous to that induced by HSV infection of the liver. Prior to i.p. injection of $CCl_4$ in olive oil, 0.2 ml of blood was collected from each of a group of 5 mice. Twenty-four hours after i.p. injection of 0.1 ml/kg $CCl_4$ in olive oil, blood was collected again, and both sets were analyzed for Alanine Amino Transferase (ALT) and Blood Urea Nitrogen (BUN). For ALT, 2 $\mu l$ serum was analyzed in duplicate with a Technicon RA 1000 and for BUN 10 $\mu l$ duplicate samples were analyzed with a Beckman Astra 8. Mice were sacrificed by cervical dislocation and the liver and kidney fixed in 10% formalin, stained with hematoxylin and eosin and examined histologically.

$^{19}F$ assay was carried out in a Nicolet-GE NT-300 NMR spectrometer, using standard techniques with a simple one-pulse sequence. The field was 7.05 Tesla (T) and the frequency was 282 megahertz. Depending upon the volume of the sample available, it was placed in either a 5 mm or 12 mm diameter tube, which was usually not spun. Both whole liver and liver homogenates were placed in 2 ml of a 2:1 v/v mixture of $D_2O$: m- hanol which inactivated HSV, permitted field homogeneity to be optimized and provided field-frequency lock for time averaging. A five-second cycle time was used with a tip angle of 60°. Sweep width was 5000 Hz and 64K data points were collected. Concentration of $^{19}F$ in a sample was evaluated by comparing the electronically integrated area of the resonance peak, after application of 10 Hz line broadening and Fourier transformation of the free induction delays using a 1280 computer, to that of standards containing 10, 50, or 100 µg/ml TFT Instrumental reproducibility of the calculated areas was checked by comparing the integral for the 40 µg/ml standard to that calculated from a scale setting obtained with a 100 µg/ml standard. In the calculation of TFT concentration, appropriate allowances were made for the dilution of the sample or for the size of the organ in the sample tube, as well as for the TFT extracted from the organ by the surrounding medium.

Because of the very wide variation in TFT levels and their relationship with viral titers above $10^6$ pfu/g liver, it could not be assumed that TFT levels were normally distributed among HSV infected mice. Therefore, data were analyzed by the non-parametric Mann-Whitney U test.

Table 1 shows the results of a representative experiment in which TFT levels and viral titers were measured in the livers of HSV-2 infected and uninfected 4–6 week old CBA/J mice. Infected mice had a TFT mean ±SE of 110.1+52.7 µg/g liver, compared with 14.7+7.7 µg/g liver for uninfected mice, $p=0.014$, Mann-Whitney U.

$CCl_4$ was selected as a control for the effect of non-specific hepatic damage, because data in the literature suggested that it was essentially a pure hepatotoxin, with no effect on renal function. At a dose of 0.2 ml/kg in olive oil injected i.p., overwhelming hepatic necrosis results a day later, with ALT levels in blood typically in the range of 20,000–30,000 IU/ml (See Table 2). As shown by the BUN, there is no significant alternation in renal function. Histologically, there is a dose related centrilobular necrosis, which at 0.2 ml/kg is massive, but at 0.0 ml/kg is more localized and less extensive. Preliminary experiments were then carried out to determine the average ALT levels of HSV-2 infected mice on day 3 at the time higher levels of TFT were found in the liver. On day 3 following i.p. injection with $4-6\times10^6$ pfu HSV-2, 4 mice had an ALT mean ±SD of 3554±781 IU/ml blood. A dose response curve of $CCl_4$ hepatitis had shown that between 0.015–0.02 ml/kg $CCl_4$ would lead to ALT levels of 500–5000 IU/ml blood. Therefore, $CCl_4$ was used at a dose of 0.02 ml/kg.

FIG. 1 shows that there was essentially no difference in blood levels of TFT at 45 minutes after i.v. injection, and no measurable blood levels of TFT at 2 hours among any of the groups. HSV-2 infected mice had significantly higher levels of TFT in their livers at both 2 and 3.5 hours after i.v. injection of TFT, whether compared with uninfected or $CCl_4$ treated mice.

If TFT levels in liver were due to accumulation in HSV infected liver cells, then the higher the HSV titer/g liver, the higher the TFT level should be. The relationship between HSV-2 pfu/g liver and TFT concentration/g liver among infected mice is illustrated in 2 separate experiments in FIG. 2. Linear regression showed a correlation coefficient of $r=0.72$, $p<0.05$ in one experiment (O's) and $r=0.99$, $p<0.05$ in the second (■'s). A similar relationship was also observed among infected mice studied at 3.5 h after receiving TFT as well as those receiving the higher dose of 160 mg/kg TFT shown in Table 1.

Sufficient material was available from 4 mice/group to measure $^{19}F$ levels by NMR spectroscopy of the whole liver under conditions as described. The results are shown in Table 3 compared with the HSV pfu/g liver where applicable and the TFT levels as measured on a small portion of same samples by HPLC. By linear regression, the correlation between HPLC and NMR was $r=0.91$, $p<0.0005$.

FIG. 3 shows actual $^{19}F$ NMR tracings of A) the 40 µg/ml standard, B) liver homogenate from an HSV-2 infected mouse 3.5 hours after i.v. injection of 100 mg/kg TFT; the area under the peak corresponds to 11 µg/g liver C) liver homogenate from a $CCl_4$ treated mouse 3.5 hours after i.v. injection of 100 mg/kg TFT and D) liver homogenate from an uninfected mouse 3.5 hours after i.v. injection of 100 mg/kg TFT.

Figure 4:
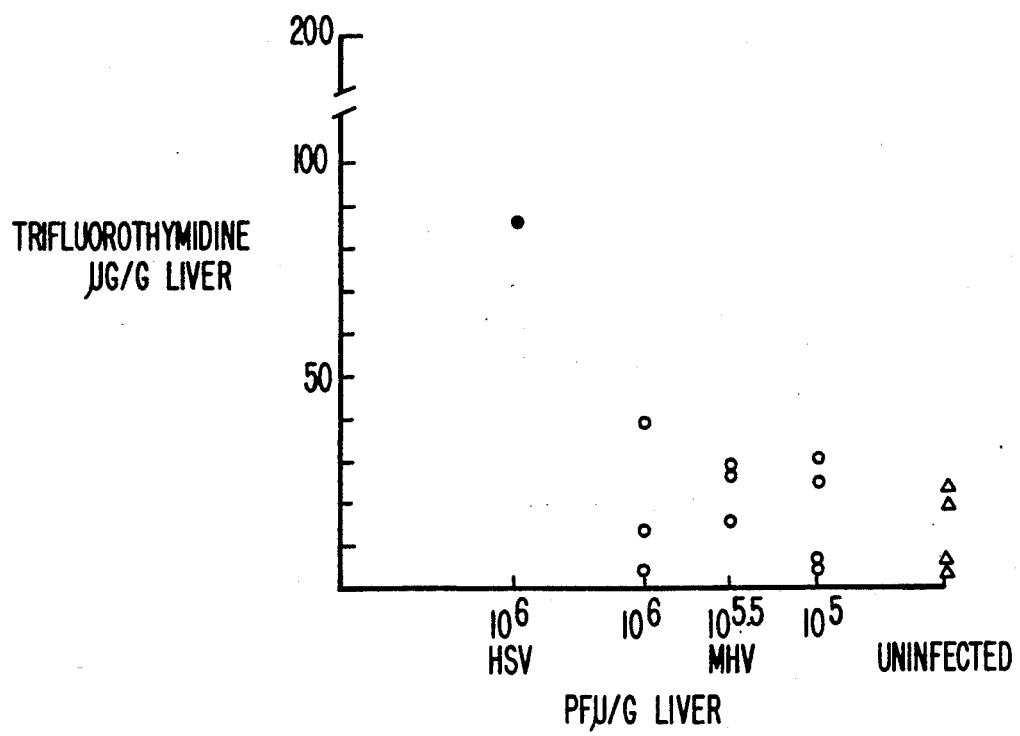

As a further specificity control 10 CBA mice were infected with murine hepatitis virus (MHV-A59), a coronavirus which does not contain thymidine kinase. As shown in FIG. 4, there was no increased concentration of TFT in livers of 10 MHV infected mice 2 h after i.v. injection of TFT, compared with the levels found in uninfected mice in the same experiment. In contrast, the 2 HSV-2 infected mice with titers of $10^6$ pfu HSV/g liver, had strikingly elevated levels.

Significantly higher levels of TFT were observed in the livers of HSV-2 infected mice, as compared with those of either uninfected mice or mice treated with $CCl_4$. The effect was repeatedly demonstrated, and correlated with the level of HSV-2 infection. Since blood levels among HSV-2 infected mice were similar to or even lower than those of uninfected mice or $CCl_4$ treated mice, it seems unlikely that delayed excretion or otherwise altered pharmacokinetics could account for the higher levels of TFT observed in the HSV-2 infected livers. Non-specific accumulation due to hepatic damage seems unlikely as well in view of the results in $CCl_4$ hepatitis.

Nuclear magnetic resonance spectroscopy was used herein to measure levels of $^{19}F$. Since there is essentially no tissue background level of fluorine, the area under the curve is directly related to a standard and is used to estimate tissue levels of TFT. TFT levels in the range of 50–100 µg/g tissue were readily detected, and even at the 1:6 dilution used, required only 10 min acquisition time, albeit at a high field strength of 7.05 T. Although the highest field strengths used diagnostically in humans are about 2 T, $^{19}F$ NMR surface coil technology has sufficient sensitivity in this range of field strength. For example, a Biospec system operating at 94 MHz was used to investigate metabolites of 5-fluorouracil (5 FU), and had a detection limit of 0.1 µmol/g in a mouse liver and a mouse tumor with 10–20 min acquisition times (manufacturer's technical information). Wolf et al reported similar studies of the behavior of 5 FU in human liver, obtaining suitable spectra in 8 min in a field of 1.5 T [Wolf et al, In: Abstracts of the Society of Magnetic Resonance in Medicine, 5th Annual Meeting, Montreal, 1986.].

One interesting finding was that the higher levels of TFT could be found in the livers of HSV-2 infected mice on day 2 as well as day 3 following HSV-2 infection. Here, the viral titers were quite low ($10^3$/g liver) compared with those in mice demonstrating the TFT accumulation on day 3, ($\geq 10^6$ pfu/g liver). ALT levels in blood in mice 2 days after HSV infection were also much lower, compared with day 3, and were in the range of 500 IU/ml blood; but data was only available from a small number of animals. Since the HSV induced TK is maximally produced approximately between 7-15 hours after infection [Kit et al, Symp. Quant. Biol., Vol. 39, pp. 703-715 (1975); Fong et al, J. Virol. Vol. 34, pp. 644-649 (1980)] which is before release of infectious virus, it is possible that early in the course of infection in vivo, as virus is spreading rapidly and infecting ever increasing numbers of new cells, higher levels of TK are present relative to the number of infectious virions, resulting in greater uptake of TFT per infectious unit.

In summary, highly elevated levels of TFT were observed in livers of HSV-2 infected mice compared with either uninfected or $CCl_4$ treated mice. There was good correlation between TFT levels in liver tissue and HSV-2 titers in the same tissues. Neither altered pharmacokinetics, nor non-specific liver damage could account for the observed drug accumulation. NMR spectroscopy has the sensitivity to detect high levels of TFT readily, and thus offers a potentially non-invasive method for the diagnosis of visceral HSV infection.

TABLE 1

TFT concentration in livers of mice infected with 160 mg/kg TFT I.V. and sacrificed at 2 hours.

| INFECTED | | UNINFECTED |
|---|---|---|
| Viral titer (PFU/g liver) | Conc. of TFT (μg/g liver) | Conc. of TFT (μg/g liver) |
| $1.1 \times 10^7$ | 266.6 | 36.5 |
| $2.4 \times 10^6$ | 60.2 | 2.5 |
| $1.1 \times 10^6$ | 74.6 | 14.3 |
| $3.4 \times 10^3$ | 38.9 | 5.6 |
| Mean* | 110.1 | 14.7 |

*p = 0.014 Infected vs. Uninfected, Mann Whitney U, see Methods for explanation.

TABLE 2

Blood levels of Blood Urea Nitrogen and Serum Alanine Aminotransferase levels in Carbon Tetrachloride and Herpes Simplex Virus-2 treated CBA/mice

| Treatment | BUN* mg/dl | Mean ± SD ALT+ IU/L |
|---|---|---|
| $CCl_4$ | | |
| Pre treatment (N = 5) | 10.4 + 2.7 | 28.2 ± 13.8 |
| 24 h post treatment (N = 5)≠ | 6.4 ± 2.3 | 28112 ± 6086 |
| 24 h post treatment (N = 12)§ | ND[11] | 18950 ± 7526 |
| HSV-2 | | |
| 48 h post infection | ND | 500 |
| 72 h post infection (N = 4) | ND | 3554 ± 781 |

*10 μl serum, BUN measured with the Beckman Astra 8
+2 μl serum, ALT measured with the Technicon RA 1000
≠Mean ± SD of the BUN and ALT prior to $CCl_4$ treatment and from the same mice 24 hours later, $CCl_4$ used at 0.2 ml/kg i.p.
§Mean ± SD of the 12 $CCl_4$ treated mice shown in FIG. 1, 45 minutes (N = 4) 2 h (N = 4) and 3½ h (N = 4) after receiving 100 mg/kg TFT, $CCl_4$ used at 0.02 ml/kg.
[11]ND = Not Done

TABLE 3

TFT concentration (μg/g liver) measured by HPLC and $^{19}F$ NMR 2 hours after intrajugular injection of 100 mg/kg TFT in CBA/J mice

| | TFT μg/g Liver | | |
|---|---|---|---|
| | Viral Titer* | HPLC+ | NMR |
| HSV-2 Infected | | | |
| #1 | $7.5 \times 10^6$ | 152.1 | 90 |
| #2 | $6.6 \times 10^6$ | 149.1 | 182.5 |
| #3 | $6.1 \times 10^6$ | 38.9 | 25 |
| #4 | $3.6 \times 10^6$ | 63.6 | 55 |
| Uninfected | | | |
| #1 | N/A | 16.0 | 45 |
| #2 | N/A | 3.5 | 0 |
| #3 | N/A | 13.8 | 20 |
| #4 | N/A | 9.9 | tr§ |
| $CCl_4$ Hepatitis | | | |
| #1 | N/A | <1.0 | tr |
| #2 | N/A | <1.0 | tr |
| #3 | N/A | <1.0 | 0 |
| #4 | N/A | <1.0 | 0 |

*pfu/g Liver
+Correlation coefficient, HPLC vs. NMR r = 0.91, p < 0.0005.
Calculated from the area under peak at −63 ppm (relative to $CFCl_3$)
§ = trace.

DETAILED DESCRIPTION OF THE DRAWINGS

FIGS. 1-3 are graphic depictions of the results of Example 1.

In FIG. 1, 1 HSV-2 infected, uninfected and $CCl_4$ treated 4-6 week old CBA/J mice were injected via the jugular vein with 100 mg/kg TFT, and sacrificed at 45 minutes, 2 hours or 3.5 hours later. The figure shows the mean ±SE of the TFT concentration in blood or liver measured by HPLC as described in the methods. Most of the experiments were done on day 3 after HSV infection; day 2 after infection was not systematically studied, and is presented only for comparison.

In FIG. 2, the relationship between HSV-2 titer/g liver and TFT concentration/g liver measured by HPLC on day 3 after HSV-2 infection, 2 h (O's) and 2.5 h (■'s) following i.v. administration of TFT. Two separate experiments are shown. Data were analyzed by linear regression. For comparison, TFT levels in the livers of the 9 uninfected mice used in these two experiments were pooled and the mean ±SD shown.

In FIG. 3, representative $^{19}F$ NMR spectra was measured with the Nicolet GE NT-300 NMR spectrometer at a field strength of 7.05 T, using a 2:1 v/v $D_2O$/methanol mixture as a field-frequency lock. A) 40 μg/ml TFT standard, acquisition time ≈7 min. B) HSV-2 infected mouse, day, 3 3.5 h after i.v. administration of 100 mg/kg. Liver homogenate prepared as described in the methods. Acquisition time was ≈28 min, and TFT concentration was 11 μg/g liver by NMR C) $CCl_4$ treated mouse, 3.5 h after i.v. administration of 100 mg/kg TFT, liver homogenate, prepared as described in the methods. Acquisition time was 1.9 hours, which accounts for the low noise level. D) uninfected mouse 3.5 h after i.v. administration of 100 mg/kg TFT, liver homogenate prepared as in the methods. Acquisition time ≈28 min. Horizontal line in B represents the cumulative area under the curve.

According to the results depicted in FIG. 4, infection of CBA/J mice with MHV-A 59 showing levels of TFT in the same range as that of uninfected mice. No relationship between MHV titer and TFT level was observed. As a positive control, other CBA/J mice were infected with HSV-2 at the same time as those infected with MHV-A 59 and those infected with HSV-2 in the range of 10⁶ pfu/g liver again showed high levels of TFT in liver. Symbols used: ●=HSV-2; ○=MHV-A 59; Δ=uninfected.

We claim:

1. A method for the diagnosis of an HSV infection in a human or non-human patient, said HSV infection being characterized by the presence of HSV-induced thymidine kinase present in HSV-infected cells of said patient, said method comprising intravenously administering to said patient a non-toxic amount of an NMR-assayable ligand-labelled trifluorothymidine and allowing said ligand-labelled trifluorothymidine to become phosphorylated by said HSV-induced thymidine kinase present in said HSV-infected cells to produce a phosphorylated NMR-assayable ligand-labelled trifluorothymidine compound which is substantially non-diffusible from within said HSV-infected cells and assaying the presence or absence of accumulated said phosphorylated compound in said cells by NMR spectroscopy.

2. The method of claim 1 wherein said assayable ligand is $^{19}F$ and said assay is NMR spectroscopy of said $^{19}F$.

3. The method of claim 1 wherein said patient is human.

* * * * *

UNITED STATES PATENT AND TRADEMARK OFFICE
CERTIFICATE OF CORRECTION

PATENT NO. : 5,053,215

DATED : October 1, 1991

INVENTOR(S) : RAND et al

It is certified that error appears in the above-identified patent and that said Letters Patent is hereby corrected as shown below:

On the title page, item [75] Inventors, delete "Gainsville" and insert therefor --Gainesville--.

On the title page, item [56] References Cited, delete "Goeer" from the line pertaining to U.S. Patent No. 4,210,638 and insert --Greer--; and under "OTHER PUBLICATIONS", at line 5, delete "Hand et al." and insert --Rand et al--.

In the ABSTRACT, at line 5, delete "bby" and insert therfor --by--; and at line 9, delete "assasying" and insert --assaying--.

Signed and Sealed this

Fourth Day of May, 1993

Attest:

MICHAEL K. KIRK

Attesting Officer    Acting Commissioner of Patents and Trademarks